US011739365B2

(12) United States Patent
Yoon et al.

(10) Patent No.: US 11,739,365 B2
(45) Date of Patent: Aug. 29, 2023

(54) METAL NANOPARTICLES FOR GLUCOSE DETECTION AND GLUCOSE DETECTION METHOD USING THE SAME

(71) Applicant: Korea University Research and Business Foundation, Seoul (KR)

(72) Inventors: Dae Sung Yoon, Seoul (KR); Insu Kim, Seoul (KR); Gyudo Lee, Namyangju-si (KR); Sang Won Lee, Seoul (KR); Dongtak Lee, Seoul (KR); Jae Won Jang, Gwangju (KR); Dongsung Park, Seoul (KR); Heeju Ahn, Seoul (KR); Hyo Gi Jung, Daegu (KR); Hoo Seong Lim, Gwangju (KR); Yonghwan Kim, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 271 days.

(21) Appl. No.: 17/159,902

(22) Filed: Jan. 27, 2021

(65) Prior Publication Data

US 2021/0238649 A1    Aug. 5, 2021

(30) Foreign Application Priority Data

Jan. 30, 2020    (KR) ........................ 10-2020-0010914

(51) Int. Cl.
 C12Q 1/26    (2006.01)
 G01N 21/78    (2006.01)
 C12Q 1/28    (2006.01)

(52) U.S. Cl.
 CPC ................ *C12Q 1/26* (2013.01); *C12Q 1/28* (2013.01); *G01N 21/78* (2013.01); *G01N 2800/042* (2013.01)

(58) Field of Classification Search
 None
 See application file for complete search history.

(56) References Cited

FOREIGN PATENT DOCUMENTS

KR    10-2019-0013474 A    2/2019

OTHER PUBLICATIONS

Liu ("Self-activated in vivo therapeutic cascade of erythrocyte membrane cloaked iron mineralized enzymes", Theranostics, 2020, vol. 10 Issue 5, 2201-2214, Supplemental Material attached) (Year: 2020).*
Li ("Immobilization of glucose oxidase onto gold nanoparticles with enhanced thermostability" Biochemical and Biophysical Research Communications 355 (2007), 488-493) (Year: 2007).*
Fu ("Erythrocyte-Membrane-Camouflaged Nanoplatform for Intravenous Glucose-Responsive Insulin Delivery" Advanced Function Materials, 2018, 28, 1802250). (Year: 2018).*
Insu Kim, et al., "Surface functionalization of erythrocyte membrane on enzyme-coronated nanoparticles for highly selective colorimetric glucose assays", School of Biomedical Engineering, Korea University, Seoul, Korea, a poster presented in a poster session of 2019 Korea Biochip Conference on Nov. 13, 2019.

\* cited by examiner

*Primary Examiner* — Robert J Yamasaki
*Assistant Examiner* — Charles Zoltan Constantine
(74) *Attorney, Agent, or Firm* — Sughrue Mion, PLLC

(57) ABSTRACT

The present disclosure provides metal nanoparticles for glucose detection, including: metal nanoparticles with glucose oxidase attached; and a cell membrane isolated from erythrocytes, which surrounds the metal nanoparticles, and a glucose detection method using the same.

2 Claims, 7 Drawing Sheets

METAL NANOPARTICLES FOR GLUCOSE DETECTION AND GLUCOSE DETECTION METHOD USING THE SAME

CROSS-REFERENCE TO RELATED APPLICATIONS

This application is based on and claims priority from Korean Patent Application No. 10-2020-0010914, filed on Jan. 30, 2020 with the Korean Intellectual Property Office, the disclosure of which is incorporated herein in its entirety by reference.

TECHNICAL FIELD

The present disclosure relates to a metal nanoparticle composite for glucose detection and a glucose detection method using the same.

BACKGROUND ART

For prevention of complications that may be caused by diabetes, such as cardiovascular diseases, stroke, nerve injury and renal dysfunction, it is very important to consistently measure and control the blood sugar level of a patient. As of 2017, an estimated 425 million adults (20-79 years) were diabetic patients globally, and the International Diabetes Federation predicts that the number will increase up to 629 million in 2045. In addition, 727 billion dollars were consumed to treat diabetes for adults in 2017, which accounts for 12% of the total consumption by adults globally.

Diabetic patients measure their blood sugar levels using glucose sensors as blood glucose level-monitoring devices and determine the dosage and time of insulin administration on the basis thereof. When precise measurement of blood glucose level is necessary, five or more different sensor devices are used instead of one device to reduce the margin of error because there are differences in accuracy among individual devices.

The existing glucose measurement sensor measures glucose in short time with high precision based on an electrochemical method using glucose oxidase or glucose dehydrogenase. The enzymes facilitate the oxidation-reduction reaction of glucose in blood, and an electron-transferring substance produced during this process is reduced and provides a signal necessary for the measurement of blood glucose level. In particular, glucose is changed to D-glucono-1,5-lactone and hydrogen peroxide by glucose oxidase. But the existing sensor has the problems that accuracy is low and it has to be carried for use.

Metal (e.g., gold) nanoparticles have specific plasmonic peaks owing to the phenomenon called surface plasmon resonance (SPR), and the intensity of the peaks can be measured using a UV-Vis spectrometer. When other substances (glucose oxidase, cell membrane, etc.) are coated on the gold nanoparticles, the intensity of the plasmonic peaks is changed. Through this, it can be confirmed whether the coating has been achieved successfully.

Meanwhile, the cell membrane consists of a phospholipid bilayer and, therefore, can prevent reckless inflow of substances into the cell membrane. In addition, among various transmembrane proteins existing between the phospholipid bilayer, transmembrane transport proteins mediate the transport of specific substances into or out of cell membrane through facilitated diffusion. Cells rich in glucose transporter 1 (GLUT1) include erythrocytes, epithelial cells, cancer cells, etc. The membrane of these cells may be used as a selective filter which transports only glucose in blood into a sensor and blocks inflow of other signal-interfering substances (non-glucose sugars, uric acid, ascorbic acid, etc.). In addition, the transmembrane protein called aquaporin 1 (AQP1), which is present in the erythrocyte membrane (EM), serves to transport hydrogen peroxide existing inside the membrane selectively out of the membrane.

A method of measuring blood sugar level through a colorimetric method is based on the chemiluminescence (CL) phenomenon whereby light is emitted as a chromogenic substrate reacts with an oxidizing agent. Light is generated by horseradish peroxidase which catalyzes a redox reaction between the hydrogen peroxide produced as glucose oxidase reacts with glucose functions as an oxidizing agent and 2,2'-azino-bis(3-ethylbenzothiazoline-6-sulfonic acid (ABTS) functions as a coloring agent.

Because the glucose oxidase used in the existing glucose measurement sensor produces hydrogen peroxide by reacting not only with glucose in blood but also with a monosaccharide (galactose, fructose, mannose or xylose) or a disaccharide (maltose) having a similar molecular structure, the concentration of glucose is measured higher than the actual concentration due to higher chemiluminescence intensity. In addition, antioxidants (ascorbic acid, uric acid, cysteine, etc.) existing in the blood also lead to errors in the glucose concentration by interfering with the action of glucose oxidase.

The inventors of the present disclosure have completed the present disclosure by consistently conducting researches on a metal nanoparticle sensor capable of selectively detecting glucose only.

REFERENCES OF RELATED ART

Patent Documents (Patent document 1) Korean Patent Publication No. 2019-0013474.

DISCLOSURE

Technical Problem

The present disclosure is directed to providing metal nanoparticles for glucose detection.

The present disclosure is also directed to providing a glucose detection kit.

The present disclosure is also directed to providing a glucose detection method using the metal nanoparticles.

However, the technical problems to be solved by the present disclosure are not limited to those mentioned above, and other unmentioned problems will be clearly understood by those of ordinary skill in the art from the following description.

Technical Solution

The present disclosure provides metal nanoparticles for glucose detection, which include:
  metal nanoparticles with glucose oxidase attached; and
  a cell membrane isolated from erythrocytes, which surrounds the metal nanoparticles.

In the metal nanoparticles of the present disclosure, metal nanoparticles (core) with glucose oxidase attached are surrounded by a cell membrane isolated from erythrocytes.

In the present disclosure, the erythrocyte-derived cell membrane surrounding the metal nanoparticles is also expressed as "coating the metal nanoparticles". The technology of coating metal nanoparticles with a cell membrane is widely known in the art as an extrusion method (Gao, W., Hu, C.-M. J., Fang, R. H., Luk, B. T., Su, J. and Zhang, L. (2013), Surface Functionalization of Gold Nanoparticles with Red Blood Cell Membranes. *Adv. Mater.*, 25: 3549-3553. doi:10.1002/adma.201300638).

The metal may be any one selected from a group consisting of gold, silver, copper, aluminum, platinum, silicon, germanium, an alloy thereof and a mixture thereof, although not being necessarily limited thereto.

The cell membrane may include glucose transporter 1 (GLUT1) and aquaporin 1 (AQP1).

The glucose transporter 1 (GLUT1) serves to transport only glucose in a sample to the metal nanoparticles with glucose oxidase attached as a core and prevent the inflow of other signal-interfering substances (non-glucose sugars, uric acid, ascorbic acid, etc.).

And, the aquaporin 1 (AQP1) serves to transport hydrogen peroxide present in the erythrocyte-derived cell membrane selectively out of the membrane.

In the present disclosure, the cell membrane of erythrocytes is coated on the metal nanoparticles with glucose oxidase attached so as to physically prevent substances other than glucose from reacting with glucose oxidase attached to the metal nanoparticles. In addition, glucose transporter 1 (GLUT1), which is present in the erythrocyte-derived cell membrane in large quantities, selectively transports only the glucose present outside the membrane selectively into the membrane, and aquaporin transports hydrogen peroxide produced inside the membrane out of the membrane. Through this effect of selectively blocking interfering substances and diffusing hydrogen peroxide, the effect of interfering substances can be excluded and a platform wherein hydrogen peroxide necessary for chemiluminescence can be produced depending on the glucose concentration in the cell membrane can be provided. As a result, the accuracy of glucose detection is improved.

The metal nanoparticles of the present disclosures for glucose detection function as a biosensor for glucose detection.

In another aspect, the present disclosure provides a glucose detection kit including the metal nanoparticles.

The kit may further include a peroxidase and a chromogenic substrate.

The chromogenic substrate may be 3,3',5,5'-tetramethylbenzidine (TMB), 2,2'-azino-bis(3-ethylbenzothiazoline-6-sulfonic acid) (ABTS), 3,3'-diaminobenzidine (DAB) or o-phenylenediamine (OPD), although not being necessarily limited thereto.

In another aspect, the present disclosure provides a glucose detection method including:

a step of preparing metal nanoparticles for glucose detection including: metal nanoparticles with glucose oxidase attached; and a cell membrane isolated from erythrocytes, which surrounds the metal nanoparticles;

a step of mixing the metal nanoparticles with a sample;

a step of inducing a color reaction by adding a colorimetric solution including a peroxidase and a chromogenic substrate to the mixture of the metal nanoparticles and the sample; and a step of detecting color change caused by the color reaction.

The sample may be a biological sample or a non-biological sample.

The biological sample may be blood, tear, urine or sweat, and the non-biological sample may be food.

In the colorimetric solution, the ratio of the hydrogen peroxide and the chromogenic substrate may be 1:1.

The addition ratio of the metal nanoparticles, the sample and the colorimetric solution may be 2:1:1. Specifically, the addition ratio of the solution including the metal nanoparticles, the sample and the colorimetric solution may be 2:1:1 based on volume.

The solution including the metal nanoparticles may be a sodium citrate solution including the metal nanoparticles.

FIG. 2 is a schematic diagram illustrating the glucose detection process. Specifically, ① glucose included in a biological sample (e.g., blood) or food selectively penetrates the erythrocyte membrane. ② The glucose that has passed through the erythrocyte membrane reacts with glucose oxidases, thereby producing $H_2O_2$. ③ The produced $H_2O_2$ is transported out of the erythrocyte membrane by aquaporin. ④ The $H_2O_2$ reacts with horseradish peroxidase (HRP) in the sample solution, thereby reducing a chromogenic substrate (ABTS) and inducing light emission at 450 nm (via color reaction).

Advantageous Effects

The metal nanoparticles for glucose detection of the present disclosure selectively uptake glucose only using the erythrocyte membrane and glucose oxidase attached to the metal nanoparticles prevent reaction with substances other than glucose. Hydrogen peroxide produced as the glucose oxidase attached to the metal nanoparticles reacts with glucose is transported out of the erythrocyte membrane. The metal nanoparticles according to the present disclosure exclude the effect of interfering substances other than glucose and induce chemiluminescence by the hydrogen peroxide produced inside the cell membrane depending on the concentration of glucose. Accordingly, the metal nanoparticles of the present disclosure may be used as a glucose measurement sensor and a glucose measurement kit with very high accuracy.

Figure 5:
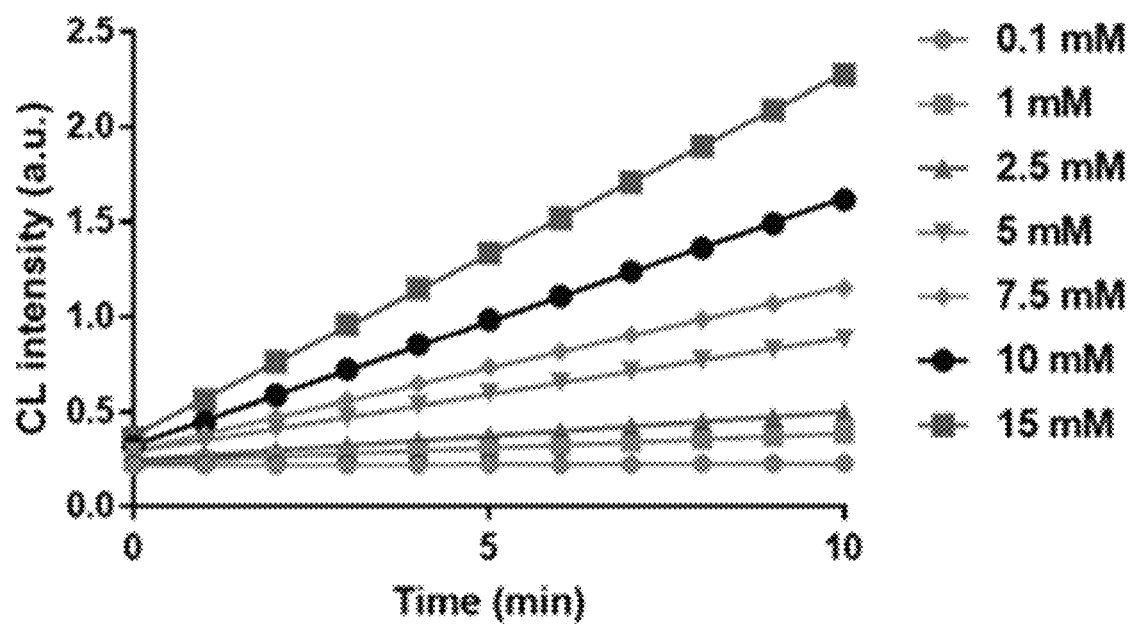
Figure 5:
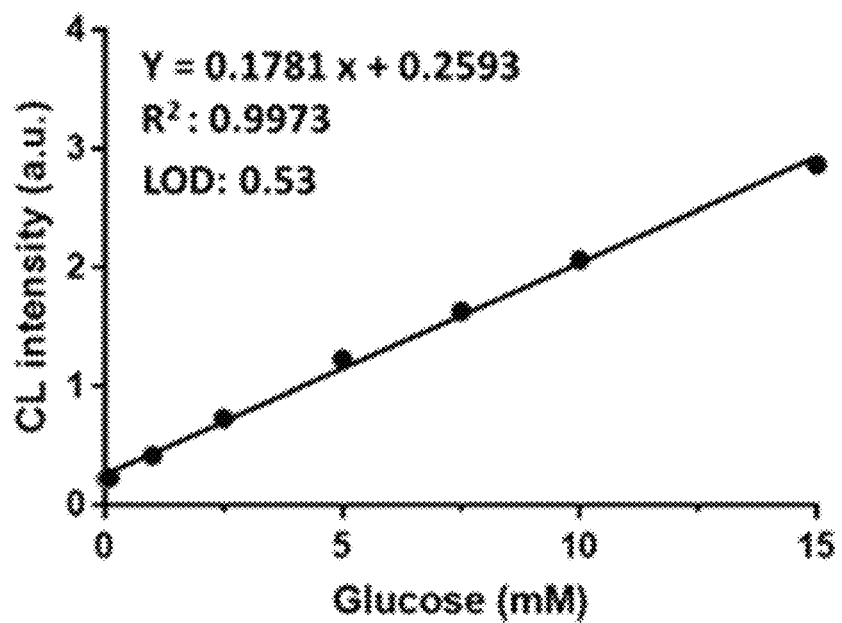

A of FIG. 5 shows a result of investigating the change in the chemiluminescence (CL) intensity of the glucose sensor EM-GOx-GNP while changing glucose concentration with 1-minute intervals. B of FIG. 5 shows the chemiluminescence intensity of the CL signals at 10 minutes, shown in 5A, depending on glucose concentration.

Figure 6:
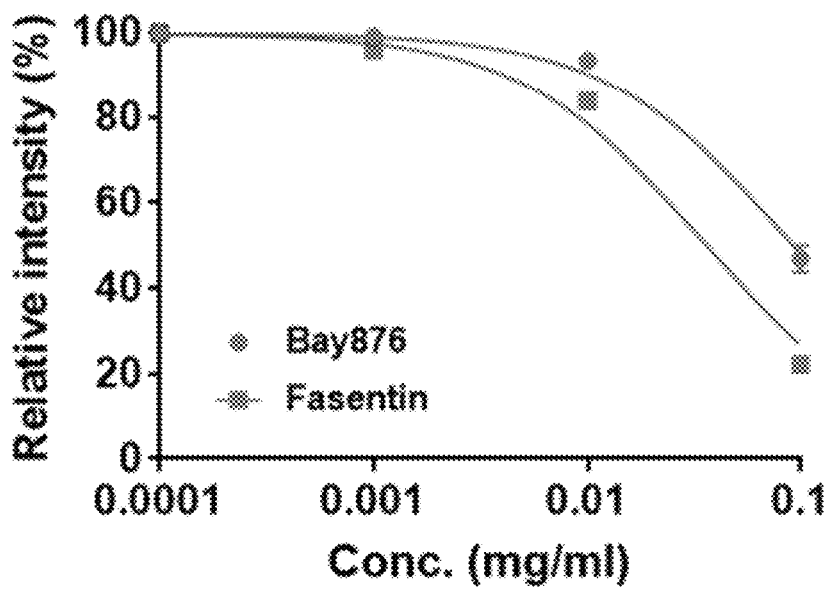

FIG. 6 shows a result of investigating the chemiluminescence (CL) signal of EM-GOx-GNP at a glucose concentration of 10 mM while changing the concentration of a glucose transporter 1 (GLUT1) inhibitor.

Figure 7:
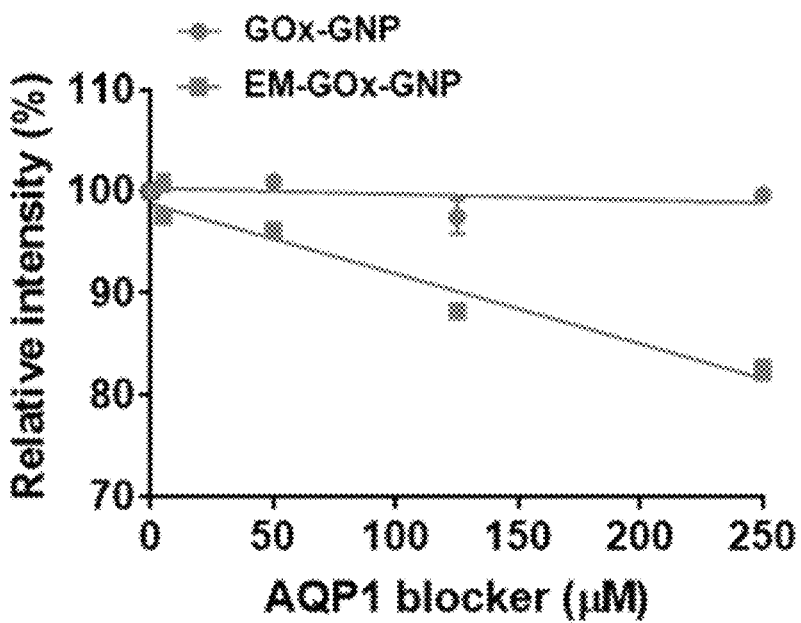

FIG. 7 shows a result of investigating the relative CL intensity (with respect to 10 mM glucose as 100%) of the glucose sensors GOx-GNP and EM-GOx-GNP when an aquaporin 1 (AQP1) inhibitor present in the erythrocyte membrane was added at a glucose concentration of 10 mM.

Figure 8:
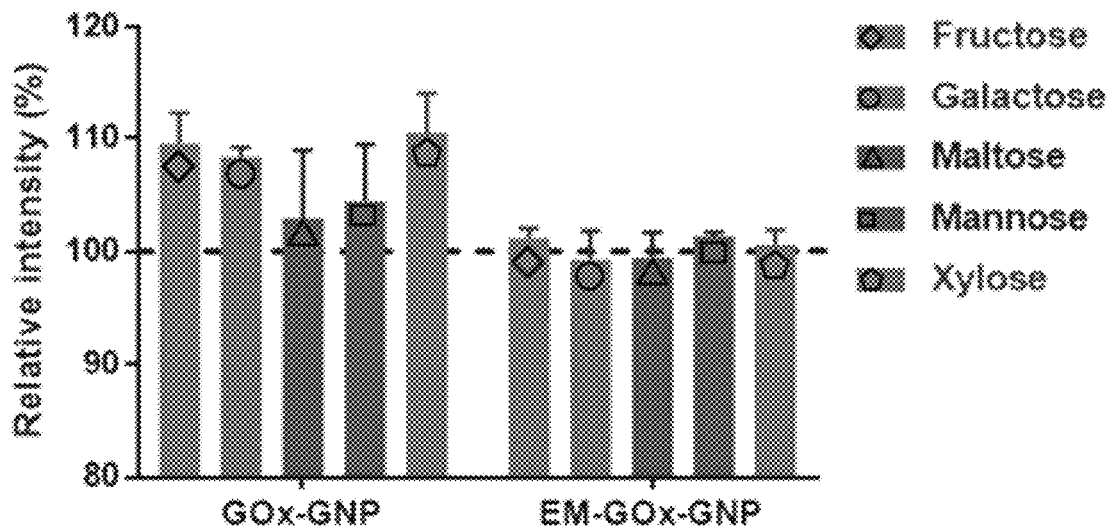

FIG. 8 shows a result of investigating the chemiluminescence (CL) intensity of erythrocyte membrane-coated EM-GOx-GNP and non-erythrocyte membrane-coated GOx-GNP when a monosaccharide (galactose, fructose, mannose or xylose) or a disaccharide (maltose) with a molecular structure similar to that of glucose was added together with glucose (10 mM).

Figure 9:
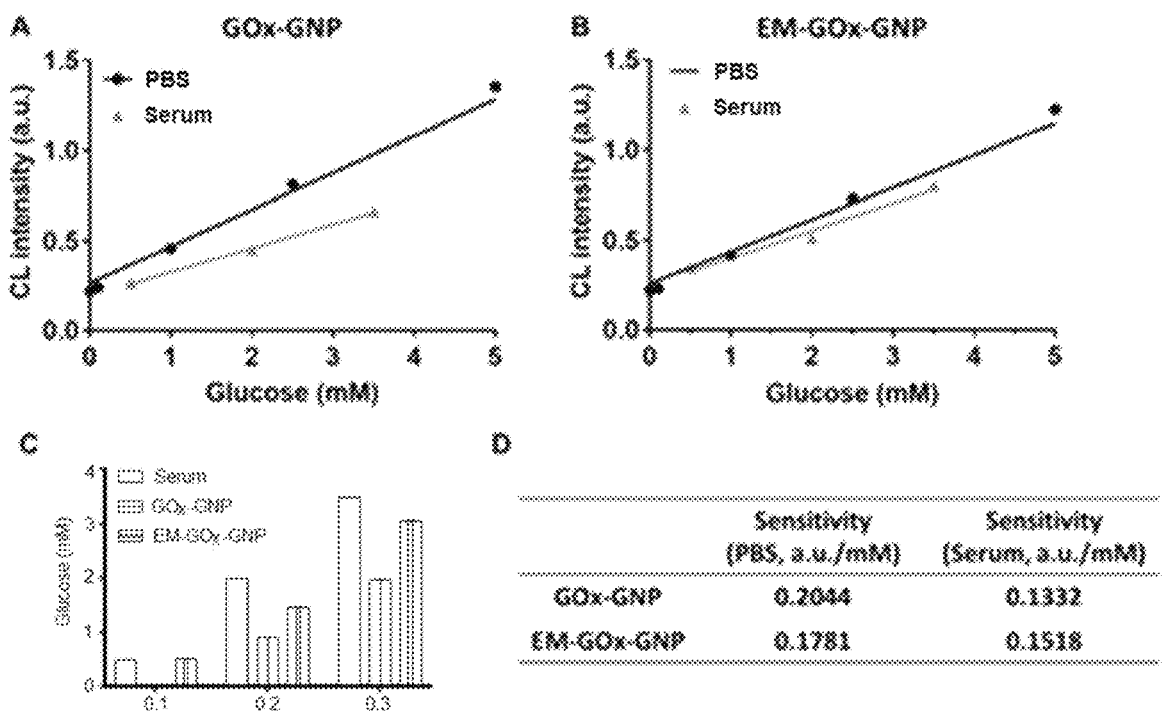

FIG. 9 shows a result of investigating the glucose detection ability of GOx-GNP and EM-GOx-GNP in human serum diluted to 10 vol %.

Figure 10:
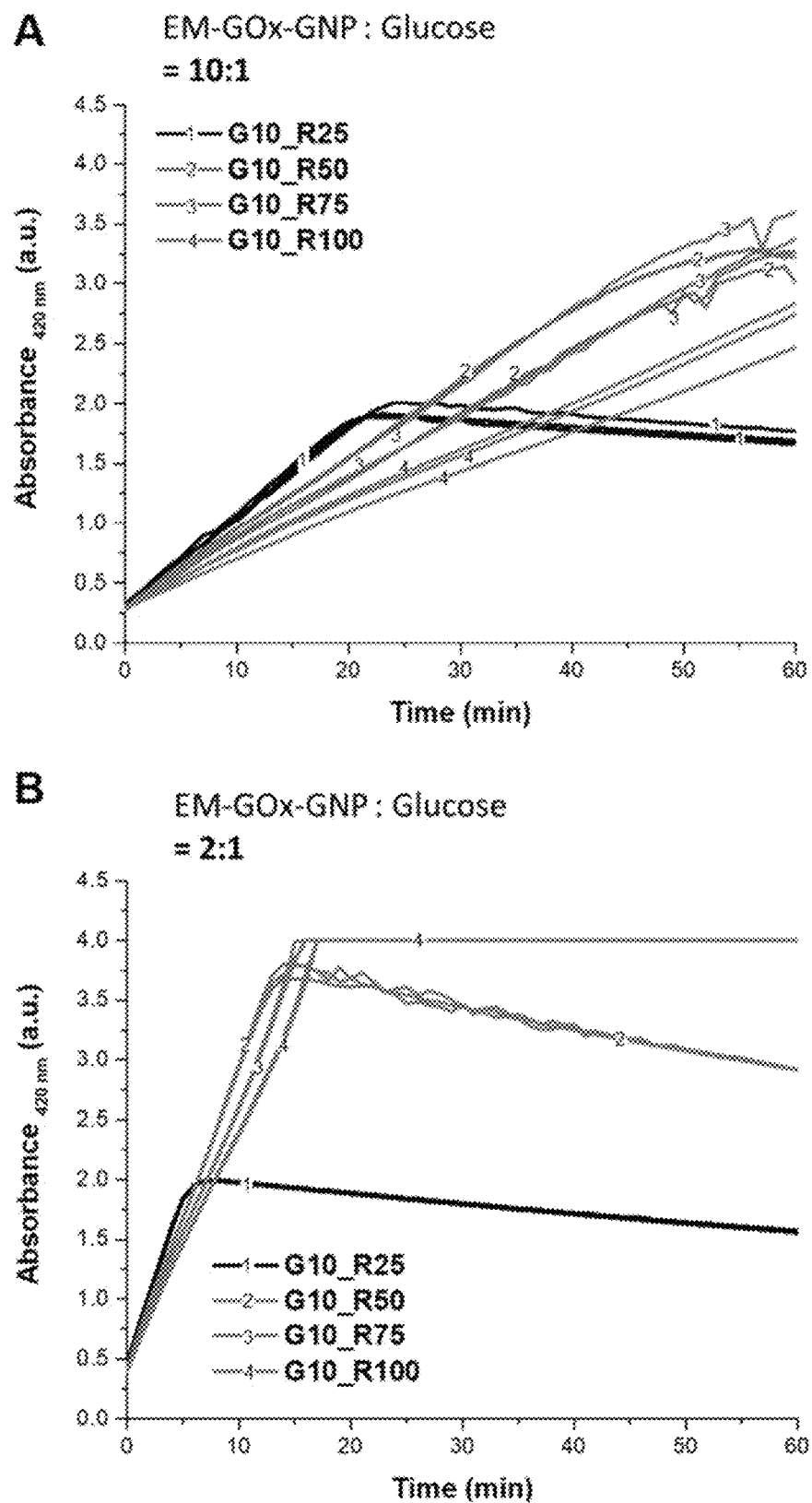

FIG. 10 shows a result of investigating absorbance depending on the contents of EM-GOx-GNP according to the present disclosure, a sample and a colorimetric solution.

BEST MODE

The present disclosure can be changed variously and may have various exemplary embodiments. Hereinafter, specific exemplary embodiments will be illustrated and described in detail referring to the attached drawings. However, the exemplary embodiments are not intended to limit the present disclosure but should be understood to encompass all changes, equivalents and substitutes included within the technical idea and scope of the present disclosure. When describing the present disclosure, detailed description of known technology may be omitted to avoid unnecessarily obscuring the subject matter of the present disclosure.

EXAMPLES

Example 1. Preparation of Metal Nanoparticle Composite for Glucose Detection 1-1. Purification of Erythrocyte Membrane Human whole blood (28-year-old, male, blood type B) was collected in an EDTA-K2 vacuum tube (Lavender) and stored at 4° C. after mixing well. The following steps were conducted in distilled water at 4° C. After isolating red blood cells (RBCs) from whole blood by continuously centrifuging at 800 g for 10 minutes, the supernatant was removed and 1×PBS was added to the precipitated RBCs for washing. For hemolysis, the collected RBCs were suspended at 4° C. for 30 minutes by adding 0.25×PBS with a volume of 5 or more equivalents of the RBCs. The prepared solution was centrifuged at 20000 g four times with 1×PBS in order to remove hemoglobin. Light pink pellets (concentrated erythrocyte membrane) were collected, suspended in distilled water and stored at −80° C. for later use.

1-2: Preparation of Metal Nanoparticles with Glucose Oxidase Attached

After adding 10 μL of glucose oxidase (GOx) (1 mg/1 mL) to 800 μL of 60-nm gold nanoparticles (GNP) and incubating under the condition of 37° C. and 5% $CO_2$ for 10, 30, 60 and 120 minutes, centrifugation was conducted at 4000 rpm for 30 minutes in order to remove the GOx not functionalized on the surface of the GNP.

Figure 1:
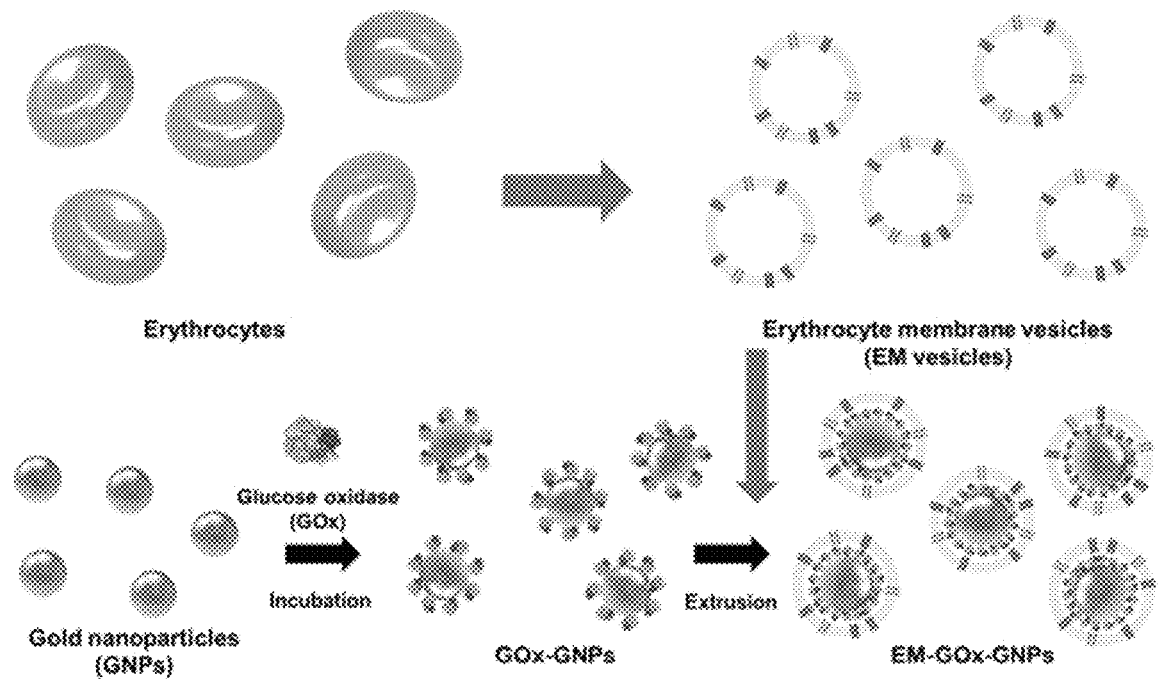
FIG. 1 shows a process of preparing the metal nanoparticles for glucose detection (EM-GOx-GNP) according to the present disclosure by coating gold nanoparticles (GNP) having a size of 60 nm as a core with glucose oxidase (GOx) and then surrounding with the erythrocyte membrane (EM). The gold nanoparticles with glucose oxidase attached are surrounded by the cell membrane extracted from erythrocytes.
Figure 2:
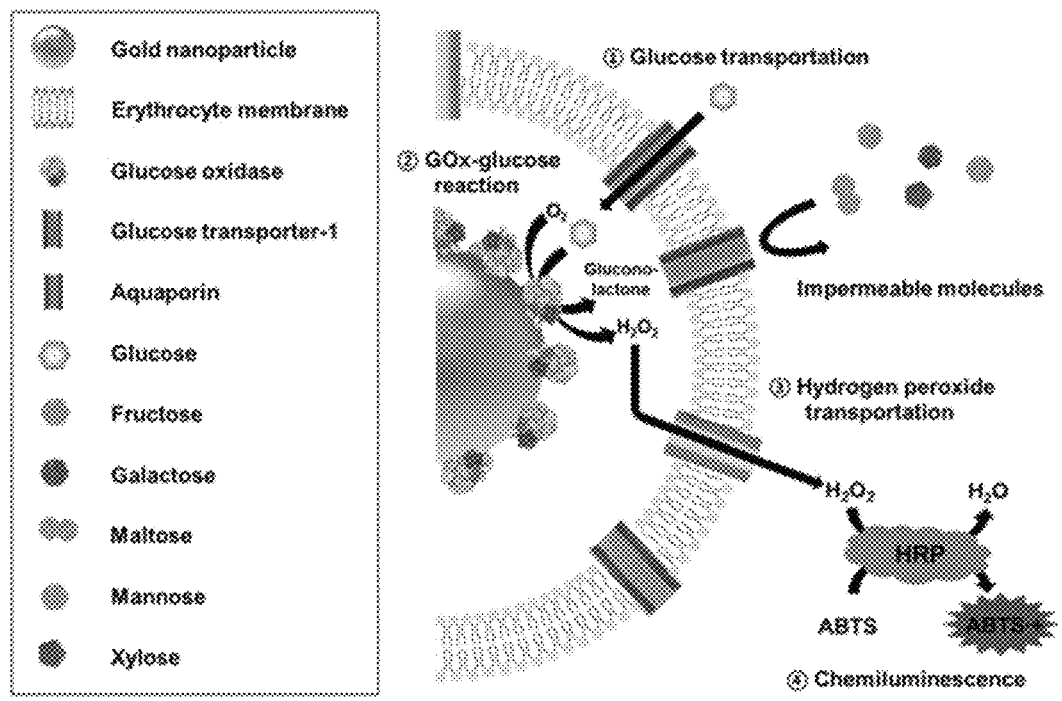
FIG. 2 is a schematic diagram illustrating a glucose detection process using the metal nanoparticles of the present disclosure.
Figure 3:
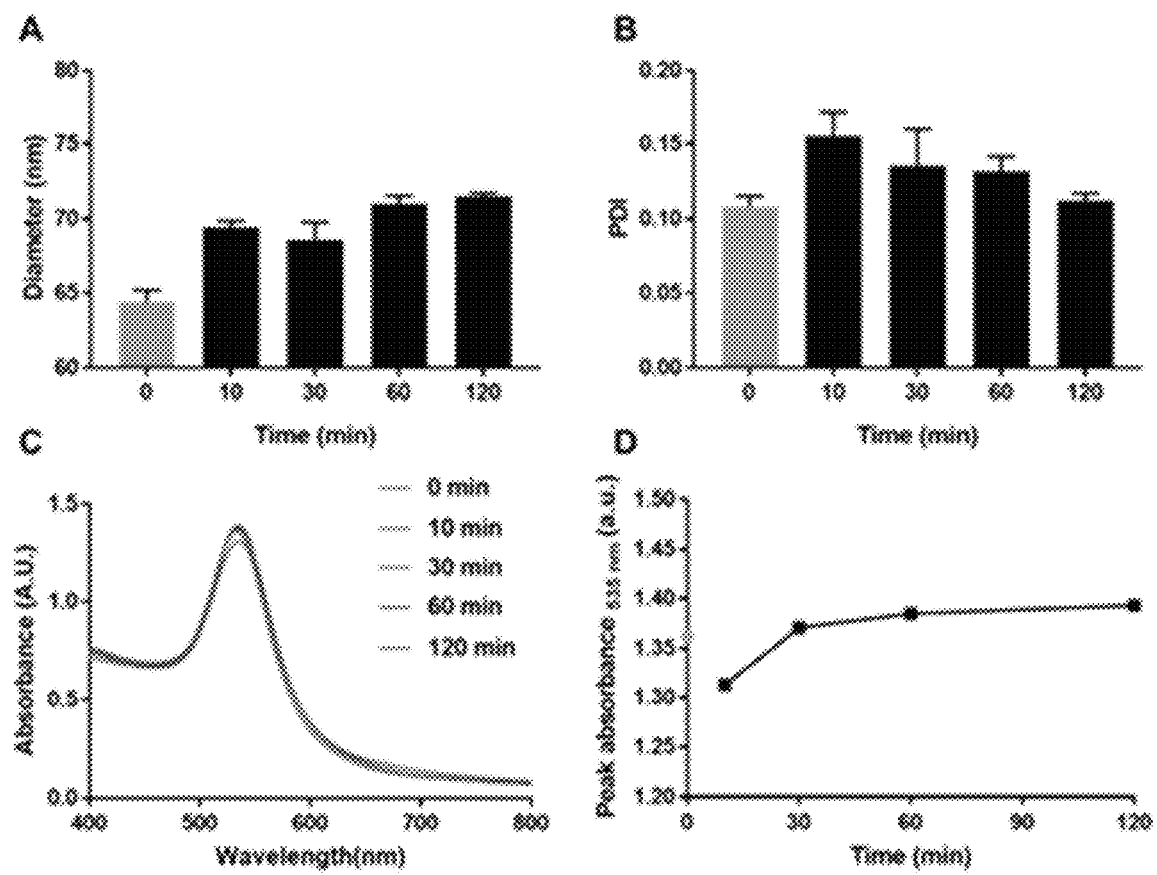
FIG. 3 shows a result of investigating the diameter and polydispersity index (PDI) of nanoparticles at 0, 10, 30, 60 and 120 minutes in order to find out the optimum incubation time for attaching glucose oxidase onto the surface of gold nanoparticles. A shows particle size depending on time, B shows the uniformity of particles depending on time, C shows absorbance depending on time, and D shows absorbance peaks (maximum) depending on time.

FIG. 3 shows a result of investigating change depending on the coating time of GOx on the gold nanoparticles (optimization of enzyme coating). From FIG. 3, it was confirmed that particle size was uniform and particle loss was decreased when the incubation was conducted for 120 minutes. Accordingly, it can be seen that the optimum time for attaching the enzyme to the gold nanoparticles is 120 minutes.

1-3: Preparation of Metal Nanoparticles for Glucose Detection (EM-GOx-GNP)

After adding 10 μL of glucose oxidase (GOx) (1 mg/1 mL) to 800 μL of 60-nm gold nanoparticles (GNP) and incubating under the condition of 37° C. and 5% $CO_2$ for 120 minutes, centrifugation was conducted at 4000 rpm for 30 minutes in order to remove the GOx not functionalized on the surface of the GNP. After the centrifugation was finished, 700 μL of the supernatant was discarded and 400 μL of distilled water and 300 μL of 1% erythrocyte membrane were added. Then, the GNP with GOx attached was coated on the erythrocyte membrane by passing through a 0.2-μm pore membrane several times according to the filter extrusion method.

Gold nanoparticles (GNP) and gold nanoparticles with only glucose oxidase attached (GOx-GNP) were used as control groups. The TEM images of GNP, GOx-GNP and EM-GOx-GNP were obtained by energy-filtered transmission electron microscopy after staining the samples with uranyl acetate, and average diameter and zeta potential were measured using a particle size and zeta potential analyzer (Zetasizer).

Figure 4:
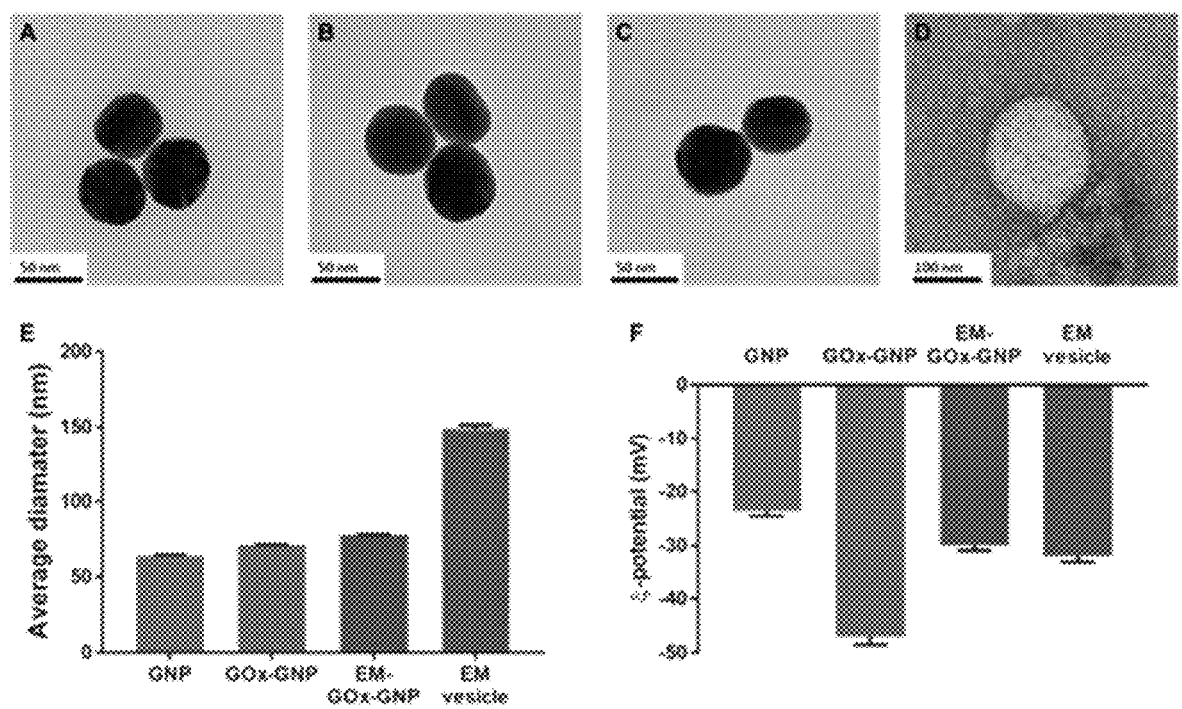
FIG. 4 shows the TEM images (A-D) of gold nanoparticles (GNP), glucose oxidase-attached gold nanoparticles (GOx-GNP) and erythrocyte-derived cell membrane-coated gold nanoparticles (EM-GOx-GNP) as well as the average diameter (E) and zeta potential (F) of the particles.

FIG. 4 shows the TEM images (A-D) of the gold nanoparticles (GNP), the glucose oxidase-attached gold nanoparticles (GOx-GNP) and the erythrocyte-derived cell membrane-coated gold nanoparticles (EM-GOx-GNP) as well as the average diameter (E) and zeta potential (F) of the particles. It was confirmed from the transmission electron microscopic image (B) that the gold nanoparticles were coated with a thin enzyme membrane and, after the coating of the erythrocyte membrane, the thickness of the thin membrane was increased by 2 nm on average (C). This visual information was confirmed by the particle size and zeta potential analysis. The particle size was increased by 7 nm on average after the coating of the enzyme on the gold nanoparticles, and was further increased by about 7 nm after the coating of the cell membrane (E). Through the zeta potential measurement, it was observed that the zeta potential became similar to the zeta potential of the cell membrane when the cell membrane was coated on the gold nanoparticles. Through this, it was confirmed that the EM-GOx-GNP was formed well (F).

Example 2. Characterization of Metal Nanoparticles for Glucose Detection 2-1. Investigation of Glucose Detection Ability For investigation of the glucose detection ability of the metal nanoparticles, a gold nanoparticle solution was prepared by adding the gold nanoparticle (EM-GOx-GNP or GOx-GNP) to a sodium citrate solution to a concentration of 0.05 mg/mL. After sequentially mixing the EM-GOx-GNP solution with a chemiluminescence detection solution (horseradish peroxidase (200 μg/mL) to 1 mM ABTS) and glucose dissolved in a phosphate buffer at different concentrations (0.1, 1, 2.5, 5, 7.5, 10 and 15 mM) with a volume ratio of 2:1:1 in a 96-well plate, chemiluminescence intensity was measured with a microplate reader for 10 minutes with 1-minute intervals, at a wavelength of 420 nm. The oxidation of ABTS induces chemiluminescence at a wavelength of 420 nm and it becomes stronger with time. When measuring with the microplate reader, the plate was shaken for 5 seconds before the first measurement and was shaken for 3 seconds prior to the subsequent measurements. The result is shown in A of FIG. 5. B of FIG. 5 shows the chemiluminescence intensity at 10 minutes for the different concentrations of glucose (0.1, 1, 2.5, 5, 7.5, 10 and 15 mM).

From FIG. 5, it can be seen that the intensity of the chemiluminescence (CL) signals of the EM-GOx-GNP increases linearly with increasing glucose concentration. Through this, the glucose detection ability of the EM-GOx-GNP (dissolved in PBS) could be confirmed.

2-2. Investigation of Glucose Detection Ability Depending on Inhibition of Glucose Transporter 1 (GLUT1)

The glucose inhibitors fasentin and BAY 876 were purchased from Sigma-Aldrich. After dissolving each inhibitor at different concentrations (0.0001-0.1 mg/mL) in dimethyl sulfoxide (DMSO) and adding the EM-GOx-GNP solution, the mixture was incubated at room temperature for 30 minutes. Then, after adding a phosphate buffer containing 10 mM glucose to the EM-GOx-GNP solution to which the fasentin or BAY 876 of different concentrations was added, chemiluminescence intensity was measured with a microplate reader at a wavelength of 420 nm. The result is shown in FIG. 6.

From FIG. 6, it can be seen that glucose transporter 1 (GLUT1) is necessary when glucose is transported selectively into the erythrocyte membrane.

2-3. Investigation of Chemiluminescence Intensity Depending on Inhibition of Aquaporin 1 (AQP1)

The AQP1 inhibitor TC AQP1 1 was purchased from Tocris Bioscience. After dissolving the AQP1 inhibitor at different concentrations (0-5 mM) in dimethyl sulfoxide (DMSO), taking 10 µL and adding to the EM-GOx-GNP solution or the GOx-GNP solution, the mixture was incubated at room temperature for 30 minutes. Then, after adding a phosphate buffer containing 10 mM glucose to the EM-GOx-GNP solution to which the AQP1 inhibitor was added, chemiluminescence intensity was measured with a microplate reader at a wavelength of 420 nm. The result is shown in FIG. 7.

FIG. 7 shows the result of investigating the relative CL intensity (with respect to 10 mM glucose as 100%) of the glucose sensors GOx-GNP and EM-GOx-GNP when the aquaporin 1 (AQP1) inhibitor present in the erythrocyte membrane was added at a glucose concentration of 10 mM. Whereas the GOx-GNP was not affected by the AQP1 inhibitor because it was not coated with the erythrocyte membrane, the EM-GOx-GNP coated with the erythrocyte membrane showed decrease in CL intensity due to inhibition of the function of aquaporin 1 (AQP1) present in the membrane. This suggests that aquaporin transports hydrogen peroxide produced in the erythrocyte membrane out of the membrane.

2-4. Investigation of Selective Glucose Detection Ability of EM-GOx-GNP Sensor of the Present Disclosure After adding 10 mM monosaccharide (galactose, fructose, mannose or xylose) or disaccharide (maltose) to a 10 mM glucose solution and mixing with the EM-GOx-GNP solution, chemiluminescence intensity was measured with a microplate reader at a wavelength of 420 nm and was represented with mean and standard deviation. The result is shown in FIG. 8.

As seen from FIG. 8, whereas the GOx-GNP not coated with the erythrocyte membrane exhibited a relative CL intensity (with respect to 10 mM glucose as 100%) of about 110% by since glucose oxidase also reacted with sugars other than glucose, the erythrocyte membrane-coated EM-GOx-GNP showed a CL intensity close to 100%. Through this, it was confirmed that glucose transporter 1 (GLUT1) present in the erythrocyte membrane selectively transports glucose only into the membrane without transporting other monosaccharides with similar molecular structure.

2-5. Investigation of Glucose Detection Ability of EM-GOx-GNP Sensor in Human Serum After adding glucose of different concentrations (0-5 mM) to a 10-fold diluted human serum solution and mixing with the EM-GOx-GNP solution or the GOx-GNP solution, chemiluminescence intensity was measured with a microplate reader at a wavelength of 420 nm 10 minutes later. The result is shown in FIG. 9.

As seen from A of FIG. 9 and B of FIG. 9, although both the GOx-GNP and the EM-GOx-GNP showed linear increase in the chemiluminescence intensity with increased glucose concentration, the EM-GOx-GNP showed a more similar tendency as PBS. That is to say, it can be seen that EM-GOx-GNP exhibits high glucose sensing intensity. Also, as can be seen from C and D of FIG. 9, it was confirmed that the glucose sensing intensity was increased because the erythrocyte membrane blocked the inflow of undesired non-glucose substances into the membrane.

2-6. Optimization of Glucose Detection Method

For optimization of the glucose detection method, absorbance was measured while changing the volume of the EM-GOx-GNP, a glucose-including sample and a detection solution (HRP & ABTS). Specifically, after fixing the volume of the EM-GOx-GNP and the sample to 100 µL and 10 µL, 25 µL (No. 1), 50 µL (No. 2), 75 µL (No. 3) or 100 µL (No. 4) of a colorimetric solution (HRP (200 µg/mL) and 1 mM ABTS dissolved in distilled water at a volume ratio of 1:1, in PBS buffer) was added to a 96-well microplate and light emission was monitored for 60 minutes at 420 nm (chemiluminescence wavelength of ABTS) with 1-minute intervals. The measurement was made three times for each volume ratio (A of FIG. 10). In addition, after fixing the volume of the EM-GOx-GNP and the glucose-including sample to 100 µL and 50 µL, 25 µL (No. 1), 50 µL (No. 2), 75 µL (No. 3) or 100 µL (No. 4) of a colorimetric solution (HRP and ABTS) was added to a 96-well microplate and light emission was monitored for 60 minutes at 420 nm (chemiluminescence wavelength of ABTS) with 1-minute intervals. The measurement was made three times for each volume ratio (B of FIG. 10). As a result, it was confirmed that, when the reaction was conducted for 10 minutes, the detection was conducted successfully when the volume ratio of the EM-GOx-GNP, the sample and the detection solution was 2:1:1 (100 µL: 50 µL: 50 µL).

Although the specific exemplary embodiments of the present disclosure have been described in detail above, it will be obvious to those having ordinary knowledge in the art that they are only preferred exemplary embodiments and the scope of the present disclosure is not limited by them. Accordingly, it is to be understood that the substantial scope of the present disclosure is defined by the appended claims and their equivalents.

The invention claimed is:

1. A glucose detection method comprising:
a step of preparing metal nanoparticles for glucose detection comprising: metal nanoparticles with glucose oxidase attached; and a cell membrane isolated from erythrocytes, which surrounds the metal nanoparticles;
a step of mixing the metal nanoparticles with a sample;
a step of inducing a color reaction by adding a colorimetric solution comprising a peroxidase and a chromogenic substrate to the mixture of the metal nanoparticles and the sample; and
a step of detecting color change caused by the color reaction,
wherein the addition ratio of the metal nanoparticles, the sample and the colorimetric solution is 2:1:1.

2. The detection method according to claim 1, wherein the sample is a biological sample.

* * * * *